United States Patent [19]

Fleeman-Hardwick

[11] Patent Number: 5,409,474
[45] Date of Patent: Apr. 25, 1995

[54] VALVED BAG AND METHOD OF MAKING SAME

[76] Inventor: Harry Fleeman-Hardwick, 1 Fieldhouse Close, Linton Hills, Wetherby, West Yorkshire LS22 4UD, United Kingdom

[21] Appl. No.: 966,033
[22] PCT Filed: Jul. 1, 1991
[86] PCT No.: PCT/GB91/01070
§ 371 Date: Dec. 24, 1992
§ 102(e) Date: Dec. 24, 1992
[87] PCT Pub. No.: WO92/00048
PCT Pub. Date: Jan. 9, 1992

[30] Foreign Application Priority Data
Jun. 29, 1990 [GB] United Kingdom ............... 9014533

[51] Int. Cl.$^6$ ............................................. A61F 5/44
[52] U.S. Cl. .................................... 604/349; 604/350; 604/351; 604/352; 604/353; 604/327; 604/322; 604/323; 604/317; 128/760; 128/767; 128/DIG. 24
[58] Field of Search ............... 604/317, 322–324, 604/327–332, 340, 344, 346–347, 349–353, 355, 403; 128/760–762, 767, 912, DIG. 24; 4/144.1–144.4

[56] References Cited

U.S. PATENT DOCUMENTS

| | | | |
|---|---|---|---|
| 2,937,645 | 5/1960 | Sachs | 604/350 |
| 3,346,883 | 10/1967 | Ersek | 604/322 |
| 3,403,410 | 10/1968 | Benzel et al. | 604/323 |
| 3,651,810 | 11/1969 | Ormerod | 604/329 |
| 3,797,734 | 3/1974 | Fleury et al. | |
| 4,790,834 | 12/1988 | Austin | 604/349 |

FOREIGN PATENT DOCUMENTS

| | | | |
|---|---|---|---|
| 0271241 | 6/1988 | European Pat. Off. | |
| 2612770 | 9/1988 | France | |
| 65308 | 11/1892 | Germany | 604/403 |
| 2249132 | 4/1973 | Germany | |
| 2515159 | 10/1976 | Germany | |
| 1245191 | 9/1971 | United Kingdom | |
| 1319442 | 6/1973 | United Kingdom | |
| 2144716 | 3/1985 | United Kingdom | |
| WO87/07137 | 12/1987 | WIPO | |

*Primary Examiner*—Randall L. Green
*Assistant Examiner*—P. Zuttarelli
*Attorney, Agent, or Firm*—Edwin D. Schindler

[57] ABSTRACT

A waterproof non-spill bag particularly for male incontinents, includes a valve which comprises a gusset (2) sealed to the side edges of the bag. In the base of the gusset small holes (7) allow liquid from the gusset to pass into the body of the bag (21) but effectively prevent it escaping if the bag is inverted. A narrow web (8) coated with self-adhesive (9) and protected by a release coated web (10), is sealed to both side edges of the bag. When the web (8) is released along a line of perforations (13), it can be wrapped around the top of the bag folded to the penis, to close it and hold it to the penis. Holes (16) surrounded by seals (17) provide for suspension and support.

24 Claims, 3 Drawing Sheets

VALVED BAG AND METHOD OF MAKING SAME

BACKGROUND OF THE INVENTION

This invention relates to a valved bag and to a method of making same, the bag being useful particularly, but not solely, as an incontinence bag.

It is known to construct valved incontinence and waste bags or pouches from polythene, waterproof paper and the like, in which a gusseted length of material is cut-off at prescribed intervals, the edges of the cut-off pieces being welded or adhered together to form a bag-within-a-bag, and small holes being made in the base of the gusset to allow urine or other liquid poured into the gusset to pass into the body of the bag. The sides of the gusset are pressed by the liquid against the sides of the bag, preventing the liquid escaping through the entry holes and so providing an effective valve. The top opening of the bag has to be wide enough for easy application to the penis but as no means for closing the top of the bag is provided, the urine can overflow if it has not drained quickly enough into the main body of the bag through the holes in the base of the gusset.

SUMMARY OF THE INVENTION

In accordance with this invention there is provided a waterproof, valved bag formed from two opposed layers of material forming opposed walls of the bag and joined together on three edges to form the side edges and the base of the bag, the bag incorporating valve means comprising a gusset or a tapered tube directed inward from an open top of the bag, the gusset having side edges joined to the side edges of the bag, the tapered tube having its wider end open and joined to the opposed walls of the bag by the edges of the opening at the top of the bag, with at least one opening in the base of the gusset or narrower end of the tapered tube to allow liquid to enter the body of the bag but preventing escape of the liquid irrespective of the orientation of the bag, and the bag further comprising an elongate web of self-adhesive coated material having a projects tag and protected by a release-coated web, the webs being aligned with and covering the open top edge of the bag by part of their width and being joined to the side edges of the bag but having one end formed with a line of weakness for tearing loose from the corresponding side edge of the bag.

The various joins may be effected by bonding (e.g. by welding or adhesive), or in some cases the join may comprise a fold in a common piece of material, as will be apparent from the description which follows.

Using for example sheet plastics such as polythene, the bag may be made from a web which is formed with a gusset, the gusset being sealed into the body of the bag by cross-weldings which form the side edges of the bag. Small openings made in the base of the gusset provide access for liquid from the gusset to the interior of the main body of the bag.

Alternatively, the bag may be made with a tapered tube insert instead of the gusset. The bag may then have two opposed sheets to form the two walls of the bag welded together on three sides. With the narrower end of the tapered tube within the bag, the wider opening of the tube is welded to the edges of the top opening of the bag. A shim, e.g. of PTFE, is inserted into the wider, open end of the tube during welding to keep this end free.

In use the bag, when the liquid has passed into the main body of the bag, cannot escape or pour out because the liquid presses the gusset or tube against the wall of the bag.

The elongate web of material, with a coating of medically-acceptable self-adhesive, is protected by another web coated with a release agent, and is aligned with and covers the top edge of the bag preferably by approximately half the width of the adhesive coating. A narrow strip on the outer edge of the web is left uncoated, in embodiments of the invention to be described herein, and a portion of this strip is punched out to leave the tag. With the uncoated side of the web facing the bag, enabling it to be welded, it is secured to each side edge of the bag by the side edge welding which form the bag. Preferably the tag is positioned adjacent one of these side edge welds. The line of weakness, e.g. a row of perforations, is made across the adhesive-coated web adjacent the tag so that the web may be torn free at that side edge of the bag but leaving it attached to the bag at its other side edge.

To provide facilities for suspending the bag as from a waist belt or for holding it against the user's leg, holes may be punched through the body of the bag. So that the liquid is retained in the bag and cannot escape through the punched holes, the holes are isolated from the interior of the bag either by welding the two walls of the bag together around the individual holes, or by positioning the holes within a watertight strip created by an additional weld a short distance inward from each side edge of the bag.

An additional or alternative means to provide support may comprise elongate webs extending across the bag and joined at each end of the side edges of the bag. Across the middle of each such web a line of weakness e.g. a row of perforations is formed, with a hole punched through the web either side of the line. When the web is torn along the line, the two halves of the web can be folded back to provide a lug at each side edge of the bag, each having a punched hole. These webs may be of a thicker or stronger material than the main body of the bag.

The bag may be formed from various waterproof materials but when made with a gusset from polythene, polypropylene, P.V.C. or other plastics materials, bags can be manufactured at speed on standard bag-making machinery with little adaptation. The size can be altered by easy machine adjustment.

As used for male incontinence, the penis extends into the interior of the gusset with the adhesive-coated web positioned behind the penis. The web is parted from one side edge of the bag using the tag to grasp and pull on, to break the line of weakness adjacent the tag, but the web held by its joint to the opposite side edge of the bag. Using this latter joint as a hinge, the web is swung round to the front of the penis, bringing the adhesive-coated side to face the bag and the penis. Surplus material in the width of the bag is folded to fit closely around the penis. With the web wrapped around the penis, half the width of the adhesive coating will hold the folds of the bag and the other half of the coating will hold the bag to the penis to effectively close the bag. The bag is easy to apply and seal in this manner.

It is found convenient to pull the release-coated web off as the adhesive-coated web is passed around the penis. When the bag is being removed, the tag, which has no adhesive coating, provides an indication of the end of the adhesive-coated web and a convenient hold for removing it. As the liquid cannot be poured out after use, preferably a very small cut is made in a skirt below a weld or join at the bottom edge of the bag, making it easy to tear into the bag. Alternatively, the bag may be cut open.

It will be found that if a patient is wearing the bag when lying down, the adhesive coating of the web is sufficient to hold the bag in place, but when the patient is standing or walking, the bag can be supported by the punched holes to suspend it from a belt or to hold it to the patient's leg.

The bag may be used for a variety of other applications where a hygienic, disposable, non-spill bag is required. The size of the drain holes in the base of the gusset, or of the opening at the narrower end of the tapered tube, can be selected as necessary. It may also be desirable to reduce the opening width of the bag as for example where it is required to insert a small diameter tube. This may be provided by welding the edges of the bag together at its top for part of its width before the adhesive-coated web is applied.

For hospital and medical use, it is advantageous if the bag is of a material which may be disposed of by grinding to reduce it to pulp or small particles before passing into the normal waste drainage system. A waterproof material used for the bag may comprise a combination of paper and plastics or waterproof resin, moistureproof cellulose film, degradable plastic, and the like. Seams may be effected using adhesives instead of welds.

Embodiments of the present invention will now be described by way of examples only and with reference to the accompanying drawings in which:

DETAILED DESCRIPTION

Figure 1:
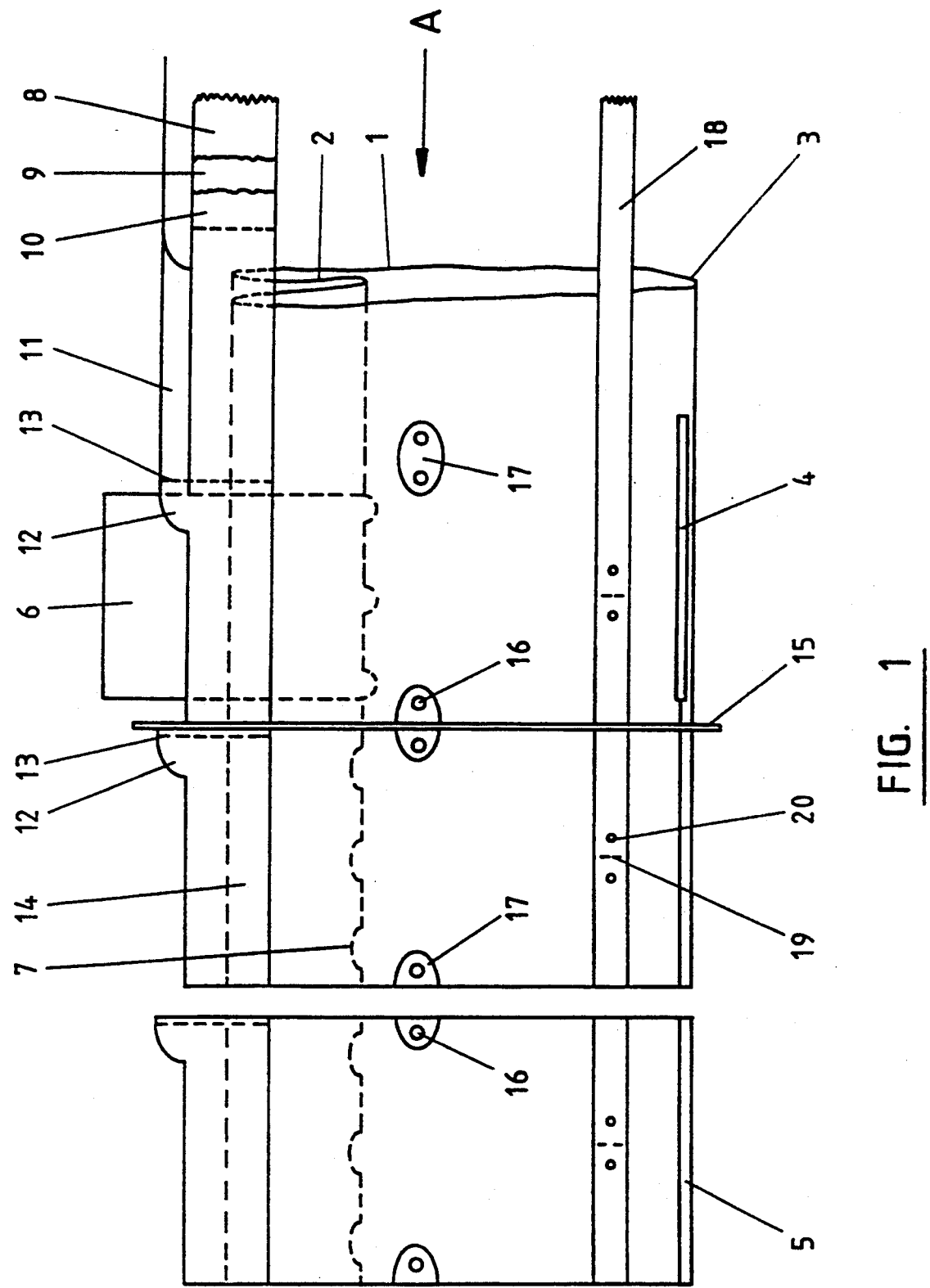
FIG. 1 illustrates a method of making incontinence and waste bags in accordance with the present invention.

Referring to FIG. 1 of the accompanying drawings, a method of making incontinence bags is illustrated using polythene sheeting by way of example. In the drawing A indicates the direction of movement of a web of material through a bag making machine. The web 1 comprises a flat sheet folded to form a gusset 2. The free edges 3 of the web 1 are welded together by a sealing bar 4 to form the base of the bag. A small cut 5 is made in the skirt formed by the weld to facilitate tearing through the base of the bag to allow liquid in the bag to be poured out: this avoids the necessity to cut into the bag to empty it. A punching plate 6 is inserted into the gusset to make small openings 7 in the base of the gusset.

Moving in the same direction A as the web 1 is a narrow or elongate web 89 which for a substantial part of its width is coated with a medically-acceptable grade of self-adhesive 9 protected by a release-coated film or web 10. On the uncoated part of the web 8, section 11 is punched out leaving a tag 12. A row of perforations 13 is formed across the web 8 adjacent the tag 12. The web 8 is then positioned to run through the bag-forming machine parallel and in line with web 1 so that it covers the top folds of web 1 for an area 14 equal to approximately half of the width of the adhesive coating 9 on web 8. A sealing bar 15 seals the side edges of the successive bags and also welds web 8 to the side edges of each of these bags before they are separated off as individual bags.

The webs 8 and 10 may be separate webs which are brought together in the bag making machine as illustrated. Alternatively they may be laminated together as a prior operation before being applied to the gusseted web 1 in the bag-making machine.

One means for providing support for the bag when in use is illustrated, comprising small holes 16 punched through the lower part of the bag adjacent its side edges. The holes 16 are surrounded by a weld 17 which isolates them from the interior of the bag to prevent any leakage. For supporting the bag as from a waist belt, the holes 16 will be higher on the bag than holes which might be required to hold the bag to the wearer's leg.

An alternative means for providing support comprises tags or lugs which are formed from a further narrow or elongate web 18, which is aligned with web 8 to run parallel with it through the bag-making machine so that it is welded to the side edges of each bag by the welding bar 15. The web 18 has cross-perforations 19 and punched holes 20, formed before the web 18 is presented to the main web 1, and positioned so that they become central across the width of the bag. When the perforations 20 are torn, the two halves of web 18, each welded to the side edges of the bag, can hinge around their welds to form support lugs at the side edges of the bag.

The width of the bag may be selected by altering the dwell time between the operations of the sealing bar 15 and as all the operations are synchronized, it will only require slight adjustment to reposition the punches for the perforations to be correctly positioned on the selected size of bag. The width of the tag may be affected unless the punch is replaced, and the length of the bag is altered by changing the width of web 1 and adjusting the sealing bar 4 accordingly.

Although the method described above is suited for use with materials such as plastics which can be welded, the same principles can be applied when using adhesive (e.g. for paper or like sheet materials). In the medical field, bags for hospital use may preferably be made of waterproof or wet strength papers and the like which can be ground to pulp in a grinding machine before passing into the normal drainage system.

Figure 2:
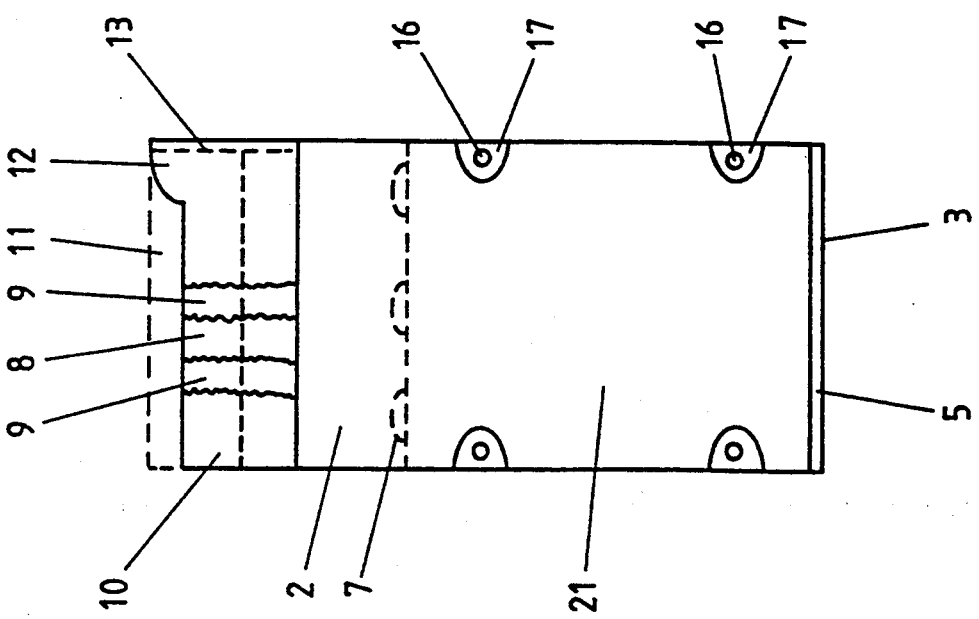
FIG. 2 is an elevation of an embodiment of incontinence and waste bag in accordance with the invention, with upper and lower support holes isolated individually from the interior of the bag.

FIG. 2 shows a bag made in accordance with the method which has been described with reference to FIG. 1. A web of polythene has been gusseted to form a body 21. The gusset 2 has small holes 7 in its base, and the gusset extends a substantial distance into the bag. The bottom edges 3 of the bag are welded together leaving a skirt in which a small cut 5 is made. Liquids which enter the body of the bag 21, through holes 7 in the base of the gusset, cannot escape because the contents will press the flap created in the bag by the gusset against the inside of the walls of the bag, effectively closing the holes 7.

Parallel with the top of the bag, web 8 with its adhesive coating 9 and protective release-coated web 10 is aligned so that approximately half its width covers the top edge of the bag. The uncoated side of web 8 faces the body of the bag which enables it to be welded to the side edges of the bag. The outlined portion 11 has been punched out to leave tag 12. Adjacent this tag is a line of perforations 13 across the web 8 which when torn open, breaks the web 8 from the edge seal of the bag at that position, leaving it held by its seal to the opposite edge of the bag. The web 8 can now hinge around the latter weld so that its adhesive-coated side will face the reverse side of the bag, where it can adhere to the top of the bag when the release-coated protecting film 10 is removed. On the penis, the folded surplus width of the bag is held together by the adhesive on half the width of the web 8 and the other half adheres to the penis. For disposal of a used bag, particularly as in a hospital, the top of the bag is folded to close it and then the folds are firmly held in place by the adhesive coating.

The holes 16 are punched through the bag to provide means of suspending the bag from the waist and holding it to the wearer's leg. Each hole 16 is surrounded by welds 17 to isolate it from the interior of the bag to prevent leakage of the contents. The small cut 5 in the skirt provides a start for a tear to be made through the bottom weld of the bag to enable the contents to be poured out.

Figure 3:
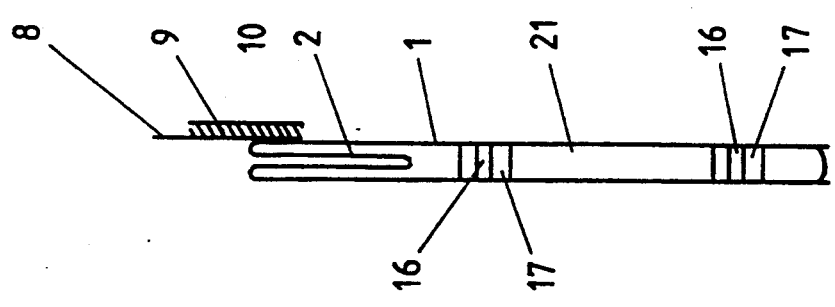
FIG. 3 is a diagrammatic longitudinal section through the bag of FIG. 2.

FIG. 3 is a section through the bag of FIG. 21 showing the single web 1 folded to provide the body portion 21 and the gusset 2 extending a substantial distance into the body of the bag. Welded to the top of the bag is web 8 with its self-adhesive coating 9 and protected by the release-coated web 10. The holes 16 are punched through the body of the bag and surrounded by welds 17 to isolate the holes from the interior of the bag.

Figure 4:
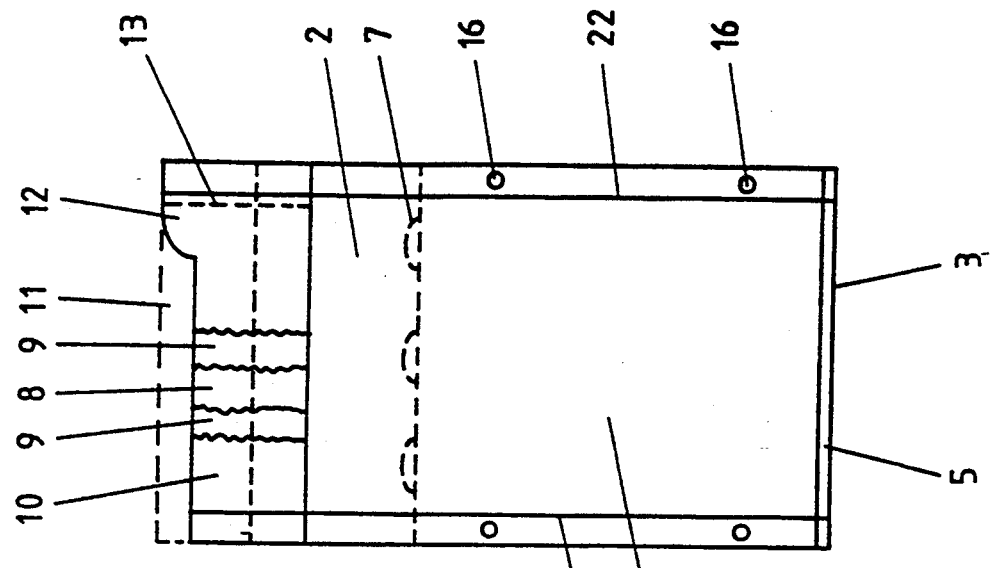
FIG. 4 is an elevation of a modified bag having the support holes isolated by longitudinal welds.

FIG. 4 shows a modified form of the bag, in which the welding 17 around the punched support holes 16 is replaced by a longitudinal weld or seal 22 a short distance inward from each side edge of the bag. Support holes 16 are formed through the welds 22 but are isolated from the interior of the bag 21, preventing any leakage through them. To maintain the desired capacity of the bag, it may be necessary to increase its width to allow for the weld margins 22 at each side edge of the bag.

Figure 5:
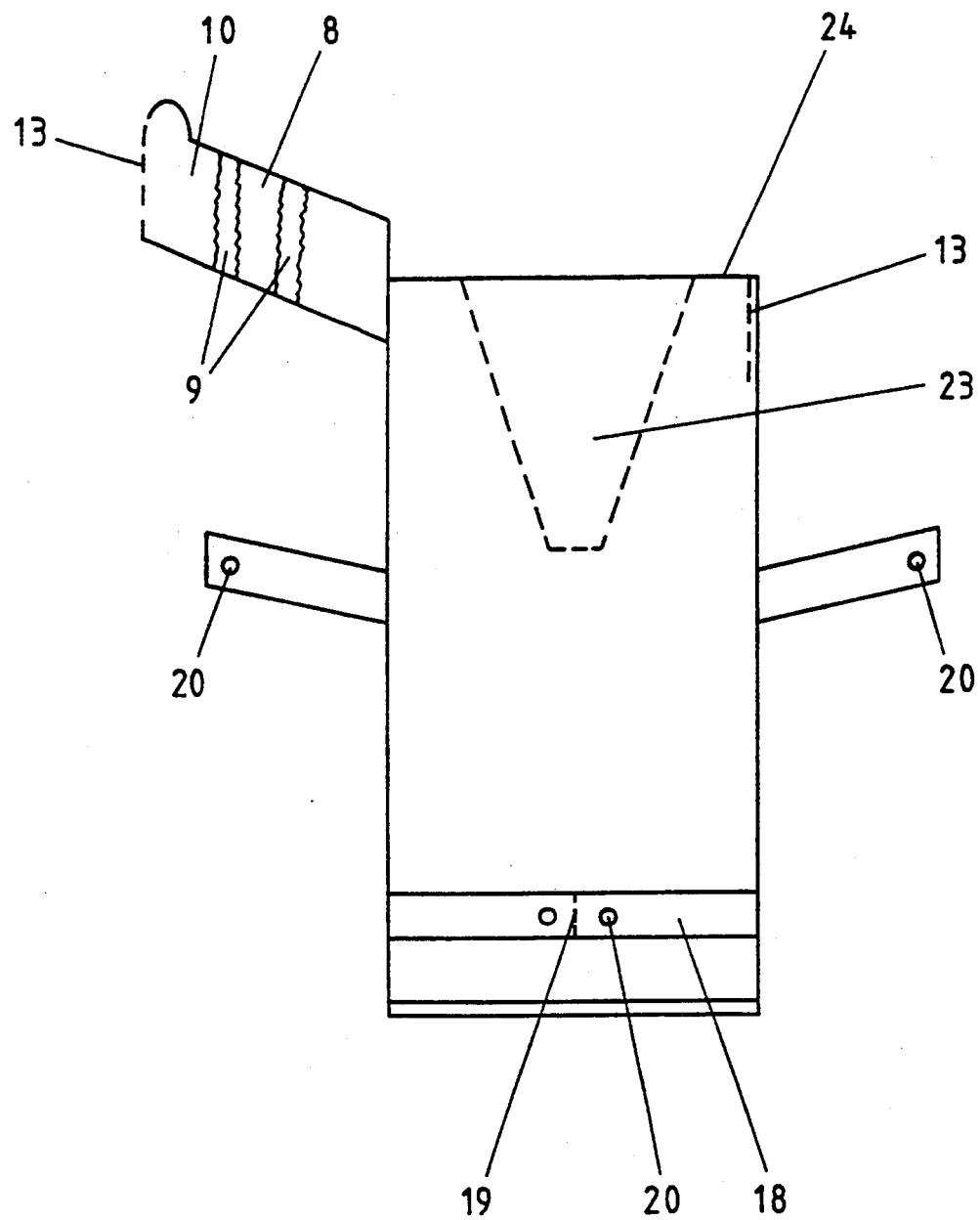
FIG. 5 is an elevation of another embodiment of incontinence and waste bag in accordance with the invention, with a tapered tube and support lugs, and showing the lugs and adhesive coated web in operative mode.

FIG. 5 shows an alternative embodiment of bag, in which the gusset 2 is replaced by a tapered tube 23 which is sealed within the top of the bag by a weld 24. In this welding operation, a P.T.F.E. coated shim is inserted into the top of the tube 23 to keep it open. In the example shown in FIG. 5, this opening to the tube 23 is not over the full width of the bag and the top edges of the bag are therefore sealed together at each side of the tapered tube. The opening width of the tube can be made to suit requirements. The bag may be formed from two separate webs of sheet material bonded (e.g. by welding or adhesive) along the bottom edge and two side edges of each bag, or by one web folded over to form the bottom edge of the bag along the fold.

With the web 8 released from one side edge of the bag by parting the perforations 13, it can hinge around its weld to the other side edge of the bag as shown. When the release-coated web 10 is removed from web 8, the adhesive coating is exposed ready for application to the bag. Web 10 has only been held temporarily to web 8 by the adhesive and this, together with the release coating, has prevented it being sealed to the side welds of the bag. One of the pairs of lugs is similarly shown ready for use after the cross perforations 19 on web 18 have been parted, enabling the lugs to hinge around their welds to the side edges of the bag, to provide for support by means of the holes 20.

I claim:

1. A waterproof, valved bag formed from two opposed layers of material forming opposed walls of the bag and joined together on three edges to form side edges and a base of the bag, to define a body having an interior thereof the bag incorporating valve means comprising a gusset having side edges joined to the side edges of the bag, and a base at the bottom thereof with at least one opening in the base of the gusset for allowing liquid to enter the body of the bag, but preventing escape of the liquid irrespective of the orientation of the bag, the bag further comprising an elongate web of self-adhesive coated material having a projecting tag and protected by a release-coated web, the webs being aligned with and covering the open top edge of the bag by part of their width and being joined to the side edges of the bag, but having one end formed with a line of weakness for tearing loose from the corresponding side edge of the bag.

2. The bag according to claim 1, wherein the adhesive-coated web is positioned to extend beyond the top of the bag by a distance equal to approximately half the width of its adhesive coating.

3. The bag according to claim 1, wherein said line of weakness of the adhesive-coated web is adjacent the tag on its outer edge.

4. The bag according to claim 1, wherein the body of the bag has holes punched therethrough, which are isolated from the interior by a surrounding bond between the opposed walls of the bag, for providing means for suspension or support.

5. The bag according to claim 1, wherein the body of the bag has holes punched therethrough, the holes being formed through the bag within margins at the side edge of the bag, which holes are isolated from the interior of the bag by longitudinal bonds, for providing means for suspension or support.

6. The bag according to claim 1, wherein said elongate web extends across a face of the bag adjoined to the side edges of the bag and having a central line of weakness with a hole each side of that line.

7. The bag according to claim 1, wherein said elongate web is of a thicker or stronger material than the material of the opposed walls of the bag.

8. The bag according to claim 1, wherein the bag includes a skirt attached to the base by a weld or bond and wherein a small cut is made in the skirt below the weld or bond along the base.

9. The bag according to claim 1, wherein said bag is formed of a waterproof material, which is disposable by a grinding machine before passing into a normal waste drainage system.

10. The bag according to claim 1, wherein the adhesive-coated web is joined to each side edge of the bag with its adhesive side facing outward from the bag.

11. The bag according to claim 10, wherein the adhesive-coated web has an uncoated strip on its outer edge.

12. The bag according to claim 11, wherein the uncoated strip on the adhesive-coated web is punched out for leaving said tag on the outer edge of said web.

13. A waterproof, valved bag formed from two opposed layers of material forming opposed walls of the bag and joined together on three edges to form side edges and a base of the bag, to define a body having an interior thereof the bag incorporating valve means comprising a tapered tube having a wider and narrower end and side edges joined to the side edges of the bag, the tapered tube having its wider end open and joined to opposed walls of the bag by the edges of the opening at the top of the bag, with at least one opening in the narrower end of the tapered tube for allowing liquid to enter the body, but preventing escape of the liquid irrespective of the orientation of the bag, the bag further comprising an elongate web of self-adhesive coated material having a projecting tag and protected by a release-coated web, the webs being aligned with and covering the open top edge of the bag by part of their width and being joined to the side edges of the bag, but having one end formed with a line of weakness for tearing loose from the corresponding side edge of the bag.

14. The bag according to claim 13, wherein the adhesive-coated web is positioned to extend beyond the top of the bag by a distance equal to approximately half the width of its adhesive coating.

15. The bag according to claim 13, wherein said line of weakness of the adhesive-coated web is adjacent the tag on its outer edge.

16. The bag according to claim 13, wherein the body of the bag has holes punched therethrough, which are isolated from the interior by a surrounding bond between the opposed walls of the bag, for providing means for suspension or support.

17. The bag according to claim 13, wherein the body of the bag has holes punched therethrough, the holes being formed through the bag within margins at the side edge of the bag, which holes are isolated from the interior of the bag by longitudinal bonds, for providing means for suspension or support.

18. The bag according to claim 13, wherein said elongate web extends across a face of the bag adjoined to the side edges of the bag and having a central line of weakness with a hole each side of that line.

19. The bag according to claim 13, wherein said elongate web is of a thicker or stronger material than the material of the opposed walls of the bag.

20. The bag according to claim 13, wherein the bag includes a skirt attached to the base by a weld or bond and wherein a small cut is made in the skirt below the weld or bond along the base of the bag.

21. The bag according to claim 13, wherein said bag is formed of a waterproof material, which is disposable by a grinding machine before passing into a normal waste drainage system.

22. The bag according to claim 13, wherein the adhesive-coated web is joined to each side edge of the bag with its adhesive side facing outward from the bag.

23. The bag according to claim 22, wherein the adhesive-coated web has an uncoated strip on its outer edge.

24. The bag according to claim 23, wherein the uncoated strip on the adhesive-coated web is punched out for leaving said tag on the outer edge of said web.

* * * * *